US005646537A

United States Patent [19]
Skaling et al.

[11] Patent Number: 5,646,537
[45] Date of Patent: Jul. 8, 1997

[54] ANTENNA-PROBE MEASURING MOISTURE IN SOIL AND OTHER MEDIUMS

[75] Inventors: Whitney Skaling, Buellton; Percy E. Skaling, Santa Barbara, both of Calif.

[73] Assignee: Soilmoisture Equipment Corp., Goleta, Calif.

[21] Appl. No.: 647,143

[22] Filed: May 9, 1996

Related U.S. Application Data

[63] Continuation of Ser. No. 398,641, Feb. 23, 1995, abandoned, which is a continuation of Ser. No. 142,833, Oct. 25, 1993, Pat. No. 5,420,517, which is a continuation of Ser. No. 855,950, Mar. 23, 1992, abandoned.

[51] Int. Cl.⁶ ..................................................... G01N 22/00
[52] U.S. Cl. ........................ 324/643; 324/601; 324/632
[58] Field of Search ..................... 324/643, 601, 324/632, 534

[56] References Cited

U.S. PATENT DOCUMENTS

| | | | |
|---|---|---|---|
| 3,789,296 | 1/1974 | Caruso | 324/643 |
| 3,978,396 | 8/1976 | Inouye | 324/337 |
| 4,006,481 | 2/1977 | Young | 324/337 |
| 4,013,950 | 3/1977 | Falls | 324/332 |
| 4,502,009 | 2/1985 | Rodiere | 324/337 |
| 4,543,823 | 10/1985 | Nagy | 324/643 |
| 4,698,634 | 10/1987 | Alongi | 324/337 |
| 4,786,857 | 11/1988 | Mohr | 324/643 |
| 5,136,249 | 8/1992 | White | 324/632 |

OTHER PUBLICATIONS

Oliver: "Electronic Measurements and Information." McGraw Hill—1972—p. 63.

*Primary Examiner*—Kenneth A. Wieder
*Assistant Examiner*—Jose M. Solis
*Attorney, Agent, or Firm*—Fulwider Patton Lee & Utecht, LLP

[57] ABSTRACT

A waveguide assembly adapted for use with a time domain reflectometry device for use in measuring the moisture content in soils and other mediums. A waveguide assembly comprised of a plurality of waveguide conductors (probes) for insertion into the soil are connected to a coaxial cable. An electronic stepped pulse travels through the coaxial cable and, due to an impedance mismatch where the coaxial cable and the waveguide assembly are joined, a downgoing beginning reference wave or reflection is produced. The beginning reference wave provides a starting point for measuring the accumulated time delay as the electronic pulse continues to travel through the waveguide assembly. An ending reflection wave is created as the electronic pulse reaches the end of the waveguide assembly and transmits into the surrounding soil. The apparent dielectric of the soil may be ascertained having determined the accumulated delay time, and in turn one can ascertain the moisture content of the soil using the apparent dielectric value.

12 Claims, 2 Drawing Sheets

ANTENNA-PROBE MEASURING MOISTURE IN SOIL AND OTHER MEDIUMS

This application is a continuation of application Ser. No. 08/398,641 filed Feb. 23, 1995, now abandoned which is a continuation of application Ser. No. 08/142,833, now U.S. Pat. No. 5,420,517 filed Oct. 25, 1993, which is a continuation of application Ser. No. 07/855,950, filed Mar. 23, 1992, now abandoned.

BACKGROUND OF THE INVENTION

This invention relates generally to a probe adapted to measure the moisture in soil and other medium.

In the past, there have been a number of instruments used to measure the moisture content in soil so that farmers, ranchers, conservationists and the like could determine when to irrigate crops, plants, trees, etc. Early devices included taking bore samples of soil and placing the samples in devices that would measure the amount of moisture content in the soil. These devices generally required time consuming processes that under quickly changing conditions characterized soils either. over- or under-irrigated with the resulting loss of crops.

Other in situ soil moisture measuring devices, such as neutron source back scatter devices, are bulky and rely on radioactive elements. Radioactive devices often are costly, require specialized personnel to operate, and have to be calibrated in the field.

SUMMARY OF THE INVENTION

In contrast to the prior art described above, more recent moisture measuring devices have been devised which operate on the principles of time domain reflectrometry (TDR). In the present invention, a plurality of probes (constituting an antenna or waveguide) are inserted into soil that is to be measured for its moisture content. TDR devices produce a step-pulse signal or an impulse signal that travels through and reacts with the waveguide (probe) and surrounding soil. Due to the novel construction of the present invention, the step pulse moving down a coaxial cable and into the probe encounters an impedance mismatch at the beginning of the probe. The impedance mismatch modifies the traveling waveforms so that when the reflection co-efficient of the waveforms is taken, the impedance mismatch is seen to create a readily identifiable capacitative or "downgoing" reflection point for use in TDR devices. Using this beginning probe reference point, one can easily ascertain, using TDR techniques, the changes in velocity of propagation and accumulated delay or delta T of the wavefront through the probes, from which one may ascertain the apparent dielectric of the soil surrounding the probes. Knowing the apparent dielectric of the soil, one can ascertain the moisture of the soil. A look-up table in a TDR device correlates the computed apparent dielectric values $K_a$ with known soil moisture values for different types of soil. As measured in the time domain, the formula is as follows: $K_a = Tc^2/L$ where L=length of probes; T=delta time—"transit time" through the probe in nanoseconds; and c=speed of light in a vacuum.

DETAILED DESCRIPTION OF THE INVENTION

Figure 1:
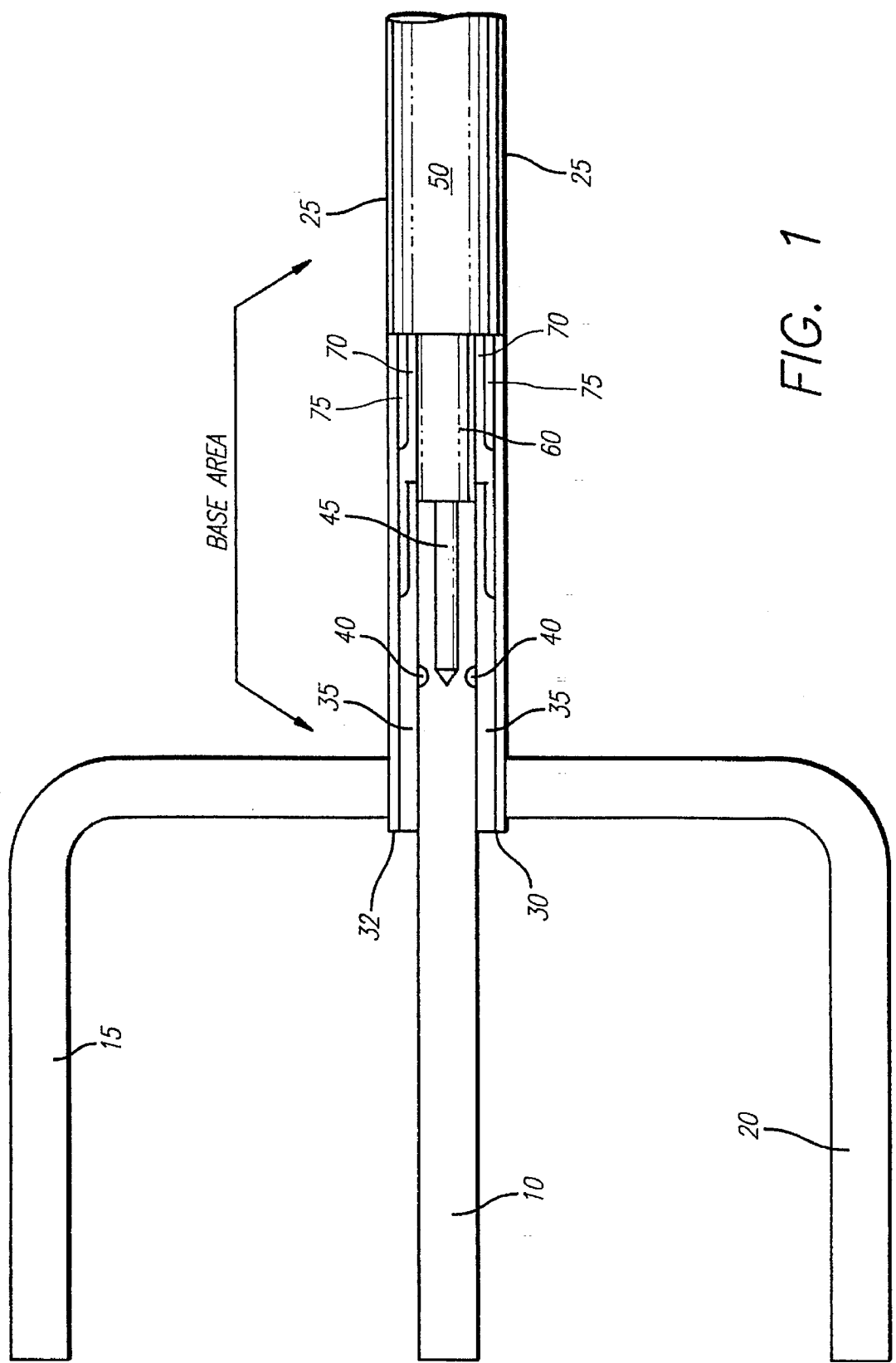
FIG. 1 is a cross-sectional view of the three-prong waveguide of the present invention.

Turning now to FIG. 1, there is shown a moisture probe (or antenna or waveguide) of the present invention. A center prong 10, a conductor preferably made of stainless steel or other electrically conductive material, is surrounded on either side by a first prong outer waveguide 15 and a second outer waveguide 20. The first and second prongs are conductors, preferably made of stainless steel or other electrically conductive materials. The three-prong conductor, as an assemblage, comprising the center prong and the first and second prong, is inserted into the soil to determine the apparent dielectric constant of the soil. Soil moisture may be ascertained from the apparent dielectric constant.

First and second prongs 15 and 20 are connected to a coaxial, stainless steel, waveguide sleeve 25. The coaxial waveguide sleeve 25 is brazed or welded to the first and second outer prongs 15, 20 at points 30, 32. The coaxial, stainless steel waveguide 25 is insulated from center conductor prong 10 by insulating outer sleeve guide 35, which may be formed of a polycarbonate material or other low dielectric plastic material. The center conductor prong 10 is crimped at crimp portion 40 to the center conductor 45 of the coaxial cable 50. Coaxial cable 50 consists of at least two conducting members. Center conductor 45 is surrounded by an outer conductor mesh 75. An insulator 60, comprised of a polyethylene dielectric, spaces the center conductor from the outer conductor. Any other suitable insulator, such as polytetraflouroethylene, commonly called TEFLON®, may be used. The outside of coaxial cable 50 is the protective outer jacket for the coaxial cable and can be made of polyvinylchloride, commonly called PVC.

A stepped inner sleeve 70, preferably made of stainless steel, or other electrically conductive material, connects outer conductor 75 with the coaxial stainless steel waveguide sleeve 25. Center conductor 10 does not contact stepped inner sleeve 70.

An important feature of the present invention is the impedance mismatch caused by the relationship between the elements in the antenna-probe area described above. As described more fully below, this impedance mismatch allows a characteristic signature to appear when applying TDR techniques to the antenna-probe, that allows one to calculate the accumulated time delay of a step pulse wave front through the probe and surrounding soil more readily, and consequently allows one to ascertain the apparent dielectric constant and moisture content of soil.

Figures 2, 3:
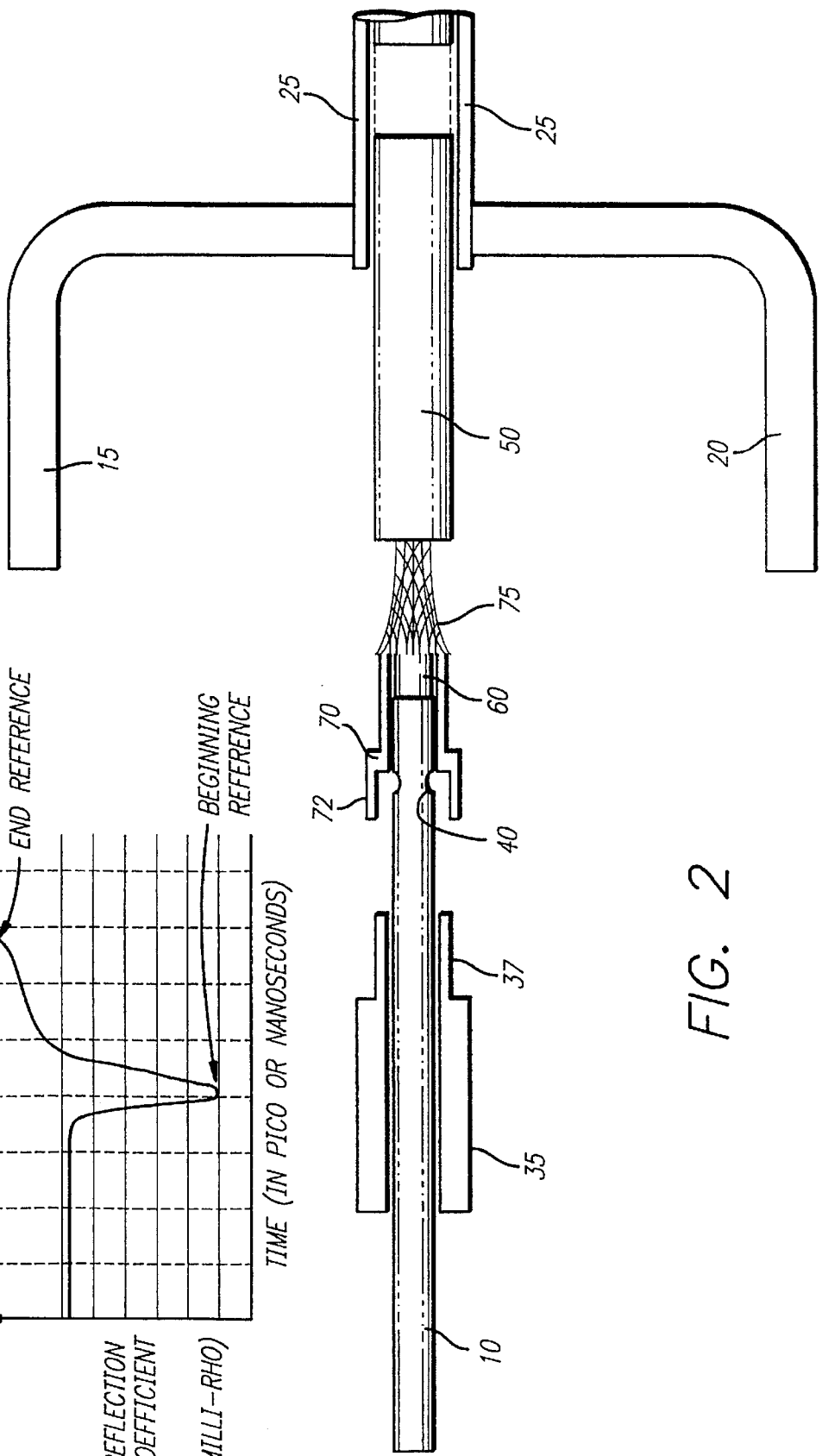
FIG. 2 is an exploded view of FIG. 1.
FIG. 3 is a chart showing values of the reflection coefficient versus distance.

Turning now to the construction of the soil moisture antenna probe of the present invention, it is seen in FIG. 2 that the probe may be constructed in a modular fashion. Coaxial cable 50, mesh 75, insulator 60, and center conductor 45 are trimmed to required lengths and the first and second waveguides 15, 20 and waveguide sleeve 25 are slipped over the left (trimmed) end of the coaxial cable. Center conductor 10 is then staked or crimped 40 to the center conductor of center conductor 45. The stepped inner sleeve 70 is fitted over the left hand side of center prong 10. Likewise, insulating outer sleeve guide 35 is slipped over the left hand side of the center prong 10. The insulating outer sleeve guide 35 and the stepped inner sleeve 70 are pushed together in a mating relationship, so that upper portion 72 of stepped inner sleeve 70 fits over lower beveled portion 37 of insulating outer sleeve 35. Next, the outer conducting member 75 of coaxial cable 50 is slipped over the stepped inner sleeve 70 and the assembled joint is pushed into stainless steel coaxial waveguide sleeve 25.

It should be noted that the above description of the assembly of the invention is merely illustrative of how the device may be assembled, and not meant to be limiting.

Turning now to operation of the present invention, it should be noted that the description of the physics behind the operation of antennas, such as the one constituting the present invention, is not always entirely clear even to those skilled in the art. The exact solution of the representation and course of electromagnetic waves in a waveguide surrounded by a complex, non-uniform dielectric such as soil is often extremely difficult to represent in the form of a closed-form, exact equation. Often the behavior of traveling waveforms is influenced by the geometry and material. composition of the material surrounding the waveguide.

In the present invention, the three prongs constitute conductive waveguides through which a traveling step pulse may traverse in both directions; that is, both towards the ends of the prongs (waveguide conductors) and back towards the base area of the probe where the construction imposed impedance mismatch exits.

In the cross-section in FIG. 1, described as the "base area," the arrangement of described items therein produce a mechanical connection and discontinuity to electromagnetic waves. In particular, an electromagnetic wavefront produced by an electronic stepped pulse or impulse traveling as a potential close to the speed of light encounters the "base area" dielectric discontinuity. Because of this unique capacitive nature of a dielectric composite formed during construction of the "base area," this area will develop a negative reflection co-efficient.

The exact nature of the creation of this negative reflection usually measured in millirho (mp) is very difficult to accurately determine. It is the impedance between the cable commonly expressed as:

$$Zo = \frac{138}{\sqrt{Er}} \log \frac{b}{a}$$

where Zo=impedance of the cable; Er=relative permitivity; a=minor diameter conductor; and b=major diameter conductor; and impedance of the base area $$Zc = \sqrt{\left[\frac{L}{c}\right]}$$

where Zc—impedance of the base area, L=inductance/unit, c=capacivity/unit and the resultant complex reflections caused by the impedance $$\Gamma = \frac{ZL - Zo}{ZL + Zo}$$

where $\Gamma$=co-efficient of reflection and Z=various impedances.

Often this negative reflection co-efficient reference point can be seen as a sharp "downgoing" notch or discontinuity on a TDR oscilloscope. Using this starting reference point, one can easily ascertain, using TDR techniques, the velocity of propagation of the waveforms through the probes. One way of doing this is to measure the time it takes for a traveling waveform that passes a given reference point to be reflected by the open end of one or more of the prongs of the probe-antenna. Given that the geometry of the probe-antenna is known, the propagation velocity of the waveform may be computed. Furthermore, the dielectric of the soil surrounding the three prongs of the device may be computed from the propagation velocity. It is known, for example, that the velocity of propagation through a medium is proportional to the square root of the dielectric of the medium.

When the prongs are inserted in soil, the soil, together with the prongs, act as an electronic circuit, albeit as a non-linear, distributed parameter electronic circuit. The transmission of waveforms in the prongs is affected by the water content of the soil. As water content increases in the soil, the apparent dielectric constant of this non-linear circuit also increases, which leads to an increased delay in the reflected waveforms from the ends of the prongs. Thus there is a relationship between apparent dielectric constant of the soil as a dielectric and soil moisture. Hence, once the apparent dielectric constant is determined from propagation velocity, the soil moisture can be computed or deduced. One way of deducing soil moisture is to employ a processor with a look-up table that stores soil moisture values associated with predetermined apparent dielectric constants, for different types of soil. A given moisture value for a given dielectric can be read directly from the table. However, other techniques to determine soil moisture from the soil dielectric constant may be employed by the present invention.

It is further noted that the relationship between moisture and the dielectric constant of soil is not a constant, but varies primarily in relation to the amount of moisture in the soil. The following table illustrates this relationship.

| Terrain | Apparent dielectric constant (Ka) |
| --- | --- |
| Soil with 10% moisture | 6.0 |
| Soil with 20% moisture | 10.0 |
| Soil with 30% moisture | 17.4 |
| Soil with 50% moisture | 32.3 |

It is believed that the antenna-probe of the present invention can measure the moisture content of soil within a 2–5 cm radius around the prongs. The prongs themselves may be about 20 cm in length. These dimensions are meant to be illustrative in nature, and are not meant to limit the invention to these figures.

Furthermore, the step-pulse used in the TDR technique of the present invention should be as square as possible and with time rises of >300 ps—10% to 90% step pulse. The sharper and squarer the step-pulse, the more accurate the TDR measurements. For example, a step pulse generator could generate a step-pulse having a rise time of 300 ps maximum (as measured between the 10% and 90% amplitude points), a topline ripple of 5% or less in amplitude (measured within 1.2 micro-seconds of the 90% amplitude point), a baseline ripple of 5% or less in amplitude (measured within 1 micro-second of the 10% amplitude point). A suitable sharp step pulse, calculated for the frequency domain would be comprised of a broad band of sinusoidal wave frequencies having a distributed power level of between 100 Khz to 3–5 Ghz.

In addition to the TDR techniques disclosed in connection with the preferred embodiment above, other techniques for measuring the apparent dielectric constant may be used with the antenna-probe of the present invention, and the specific TDR techniques are not meant to limit the practice of the invention to the specific techniques disclosed.

While specific embodiments of the invention have been described in detail, it will be appreciated by those skilled in the art that various modifications to the structure and use of the disclosed invention may be made in light of the overall teachings of the disclosure, without departing from the scope of the invention as defined by the appended claims.

We claim:

1. A time domain reflectometry waveguide assembly for measuring the moisture content in a medium, comprising:

a probe having at least two spaced apart waveguide conductors for insertion into the medium;

a coaxial cable connected to said probe for transmission of a signal of the kind used in time domain reflectometry, said coaxial cable having a center conductor, an outer conductor and an insulator spacing said inner conductor from said outer conductor, said center conductor connected to one of said waveguide conductors and the outer conductor connected to the other of said waveguide conductors, wherein a specific impedance mismatch between the coaxial cable and the waveguide conductors independent of the impedance of said medium causes a detectable characteristic reference reflection in a time domain reflectometry signal transmitted through said coaxial cable and said probe; and a processor calculating the apparent dielectric constant value of said medium based on a time delay measured in response to said detectable characteristic reference reflection, and correlating the apparent dielectric constant value with data reflecting the moisture content of the medium.

2. The waveguide assembly of claim 1, wherein said processor further includes a look-up table correlating apparent dielectric constant values with a moisture content of the medium; and the processor determines the moisture content of said medium based on the calculated apparent dielectric constant and said look-up table.

3. The waveguide assembly of claim 1, wherein said signal includes step-pulses.

4. The waveguide assembly of claim 1, further comprising an outer sleeve surrounding an end of one of said waveguide conductors and being connected to the other of said waveguide conductors, and an insulating guide disposed between said outer sleeve and said waveguide conductor end.

5. The waveguide assembly of claim 4, further comprising an inner sleeve disposed between said insulating guide and said outer conductor.

6. The waveguide assembly according to claim 5, wherein said inner sleeve has a stepped configuration.

7. The waveguide assembly according to claim 5, wherein said inner sleeve has a stepped configuration with first and second portions of different diameter, said first portion being coaxially disposed between said insulator and said outer conductor and said second portion being coaxially disposed between said insulating guide and said outer sleeve, said first portion having a smaller diameter than said second portion.

8. The waveguide assembly of claim 5, wherein the probe further includes a third waveguide conductor, and said one of said at least two waveguide conductors is located between said other of said at least two waveguide conductors and said third waveguide conductor which are both connected to said outer sleeve.

9. A method for using a time domain reflectometry waveguide assembly to measure the moisture content in a medium, comprising:

inserting a probe having at least two spaced-apart waveguide conductors of known length into a medium to be measured, and the probe includes an outer sleeve surrounding an end of one of the waveguide conductors, and an insulating guide disposed between the outer sleeve and the waveguide conductor end;

connecting a coaxial cable to the probe, the coaxial cable including an outer conductor;

positioning an inner sleeve having a stepped configuration between the insulating guide and the outer conductor;

transmitting a signal of the kind used in time domain reflectometry through the coaxial cable and the probe;

introducing a detectable characteristic reference reflection into the signal by way of a specific construction-imposed impedance mismatch between the coaxial cable and the waveguide conductors independent of the impedance of the medium being measured which causes an identifiable reference reflection in the signal transmitted through the waveguide assembly in order to mark a known location in relation to the waveguide conductors;

commencing a measurement of time delay in response to detection of the characteristic reference reflection;

calculating an apparent dielectric constant value based on the time delay; and correlating the apparent dielectric constant with data reflecting the moisture content of the medium.

10. The method of claim 9, wherein the step of introducing the characteristic reference reflection is provided by introducing a specific impedance mismatch produced by a base area defined between the coaxial cable and the waveguide conductors.

11. The method of claim 9, wherein the step of introducing the characteristic reference reflection into the signal further includes marking a beginning reference point on the waveguide conductors.

12. The method of claim 9, wherein the step of transmitting the signal includes sending a signal including step-pulses.

* * * * *